United States Patent
Fluyeras

[11] Patent Number: 5,902,296
[45] Date of Patent: May 11, 1999

[54] INCONTINENCE BRIEF WITH MOISTURE INDICATING STRIP

[76] Inventor: Alexandra Fluyeras, 5869 W Ave., Aurelia, Iowa 51005

[21] Appl. No.: 08/938,374
[22] Filed: Sep. 25, 1997
[51] Int. Cl.⁶ ........................ A61F 13/15
[52] U.S. Cl. ............................ 604/361
[58] Field of Search ................. 604/361

[56] References Cited

U.S. PATENT DOCUMENTS

| | | | |
|---|---|---|---|
| 3,731,685 | 5/1973 | Eidus | 604/361 |
| 4,738,674 | 4/1988 | Todd et al. | 604/361 |
| 4,834,733 | 5/1989 | Huntoon et al. | 604/361 |
| 5,469,145 | 11/1995 | Johnson | 604/361 |

FOREIGN PATENT DOCUMENTS

| | | | |
|---|---|---|---|
| 3810473 | 10/1989 | Germany | 604/361 |
| 94/10958 | 5/1994 | WIPO | 604/361 |

*Primary Examiner*—Robert A. Clarke

[57] ABSTRACT

A incontinent brief moisture indicator is provided including a brief formed of a moisture absorbing material. The brief includes a top waist opening and pair leg openings. The brief has a front portion, a rear portion, and a crotch portion. Next provided is an elongated transparent sleeve with a front face, a rear face, a top closed end and a bottom open end. The transparent sleeve is coupled to the brief in a vertical orientation with the bottom end extending downwardly and terminating at the crotch portion. A moisture indicator strip is situated within the transparent sleeve such that a top end thereof is situated coincident with the top closed end of the transparent sleeve and a bottom end thereof extends through the bottom opening of the transparent sleeve and is situated in communication with the moisture absorbing material of the crotch portion of the brief. During use, the strip is adapted to change color upon the detection of moisture.

2 Claims, 2 Drawing Sheets

5,902,296

INCONTINENCE BRIEF WITH MOISTURE INDICATING STRIP

BACKGROUND OF THE INVENTION

1. Field of the Invention

The present invention relates to moisture indicators and more particularly pertains to a new incontinence brief with moisture indicating strip for providing an indication of a predetermined amount of moisture within an incontinence brief.

2. Description of the Prior Art

The use of moisture indicators is known in the prior art. More specifically, moisture indicators heretofore devised and utilized are known to consist basically of familiar, expected and obvious structural configurations, notwithstanding the myriad of designs encompassed by the crowded prior art which have been developed for the fulfillment of countless objectives and requirements.

Known prior art moisture indicators include U.S. Pat. No. 4,231,370; U.S. Pat. No. 4,705,513; U.S. Pat. No. 4,931,051; U.S. Pat. No. 5,389,093; and U.S. Pat. No. Des. 354,809.

In these respects, the incontinence brief with moisture indicating strip according to the present invention substantially departs from the conventional concepts and designs of the prior art, and in so doing provides an apparatus primarily developed for the purpose of providing an indication of a predetermined amount of moisture within an incontinence brief.

SUMMARY OF THE INVENTION

In view of the foregoing disadvantages inherent in the known types of moisture indicators now present in the prior art, the present invention provides a new incontinence brief with moisture indicating strip construction wherein the same can be utilized for providing an indication of a predetermined amount of moisture within an incontinence brief.

The general purpose of the present invention, which will be described subsequently in greater detail, is to provide a new incontinence brief with moisture indicating strip apparatus and method which has many of the advantages of the moisture indicators mentioned heretofore and many novel features that result in a new incontinence brief with moisture indicating strip which is not anticipated, rendered obvious, suggested, or even implied by any of the prior art moisture indicators, either alone or in any combination thereof.

To attain this, the present invention generally comprises a brief formed of a moisture absorbing material. As shown in FIG. 1, the brief includes a top waist opening and pair leg openings each lined with a peripheral elastic seam. The brief has a front portion, a rear portion, and a crotch portion. Next provided is a thin elongated transparent sleeve having a rectangular configuration. As shown in FIGS. 2 & 4, the sleeve is formed of a front face, a rear face, a top closed end and a bottom open end. The transparent sleeve is coupled to an inner surface of the front portion of the brief in a vertical orientation. In such orientation, the top closed end is extended above the top opening and the bottom end extends downwardly and terminates at the crotch portion. Finally, a moisture indicator strip is provided having a rectangular configuration. The strip is preferably constructed from litmus paper. As shown in FIGS. 2 & 4, the moisture indicator strip is situated within the transparent sleeve such that a top end thereof is situated coincident with the top closed end of the transparent sleeve and a bottom end thereof extends through the bottom opening of the transparent sleeve. It is imperative that the bottom end of the strip reside in communication with the moisture absorbing material of the crotch portion of the brief. By this structure, the strip is adapted to change color upon the detection of moisture. It should be noted that a length of a portion of the strip that changes color is a function of the amount of moisture absorbed by the brief.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new incontinence brief with moisture indicating strip apparatus and method which has many of the advantages of the moisture indicators mentioned heretofore and many novel features that result in a new incontinence brief with moisture indicating strip which is not anticipated, rendered obvious, suggested, or even implied by any of the prior art moisture indicators, either alone or in any combination thereof.

It is another object of the present invention to provide a new incontinence brief with moisture indicating strip which may be easily and efficiently manufactured and marketed.

It is a further object of the present invention to provide a new incontinence brief with moisture indicating strip which is of a durable and reliable construction.

An even further object of the present invention is to provide a new incontinence brief with moisture indicating strip which is susceptible of a low cost of manufacture with regard to both materials and labor, and which accordingly is then susceptible of low prices of sale to the consuming public, thereby making such incontinence brief with moisture indicating strip economically available to the buying public.

Still yet another object of the present invention is to provide a new incontinence brief with moisture indicating strip which provides in the apparatuses and methods of the prior art some of the advantages thereof, while simultaneously overcoming some of the disadvantages normally associated therewith.

Still another object of the present invention is to provide a new incontinence brief with moisture indicating strip for providing an indication of a predetermined amount of moisture within an incontinence brief.

Even still another object of the present invention is to provide a new incontinence brief with moisture indicating strip that includes a brief formed of a moisture absorbing material. The brief includes a top waist opening and pair leg openings. The brief has a front portion, a rear portion, and a crotch portion. Next provided is an elongated transparent sleeve with a front face, a rear face, a top closed end and a bottom open end. The transparent sleeve is coupled to the brief in a vertical orientation with the bottom end extending downwardly and terminating at the crotch portion. A moisture indicator strip is situated within the transparent sleeve such that a top end thereof is situated coincident with the top closed end of the transparent sleeve and a bottom end thereof extends through the bottom opening of the transparent sleeve and is situated in communication with the moisture absorbing material of the crotch portion of the brief. During use, the strip is adapted to change color upon the detection of moisture.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
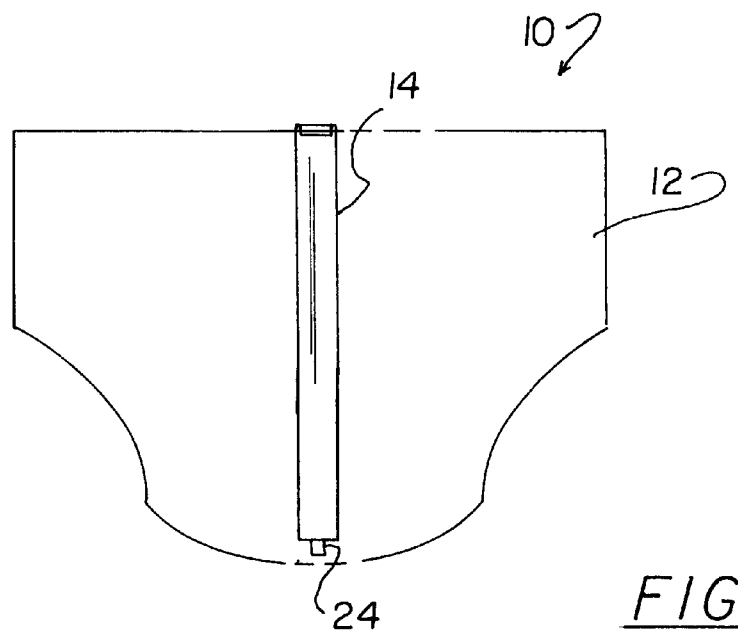
FIG. 1 is a front view of a new incontinence brief with moisture indicating strip according to the present invention.

With reference now to the drawings, and in particular to FIGS. 1 through 4 thereof, a new incontinence brief with moisture indicating strip embodying the principles and concepts of the present invention and generally designated by the reference numeral 10 will be described.

The present invention as designated as numeral 10 includes a brief 12 formed of a moisture absorbing material. As shown in FIG. 1, the brief includes a top waist opening and pair leg openings each lined with a peripheral elastic seam. The brief has a front portion, a rear portion, and a crotch portion. As an option, an outer surface of the brief may be lined with a liquid impervious plastic material.

Figure 2:
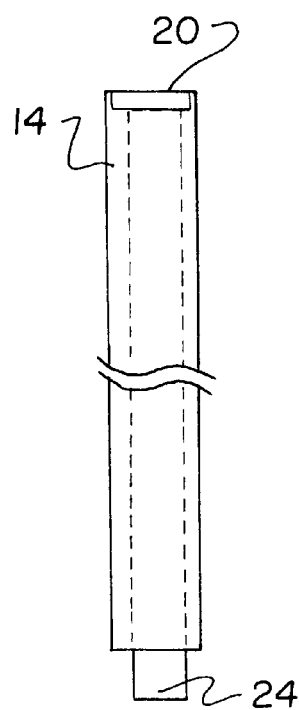
FIG. 2 is a front view of the present invention.
Figure 3:
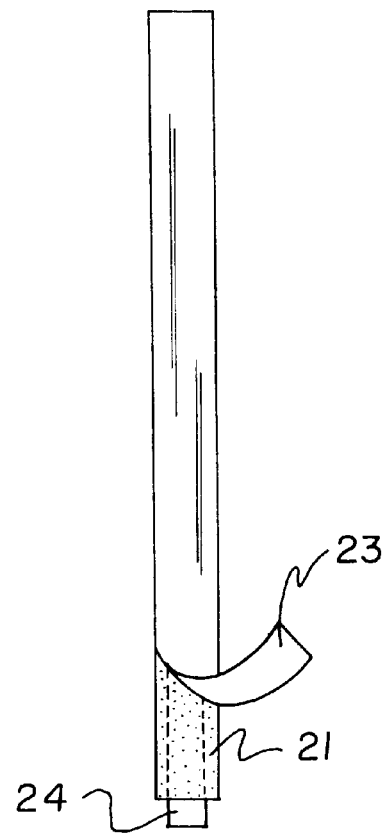
FIG. 3 is a front view of an alternate embodiment of the present invention.
Figure 4:
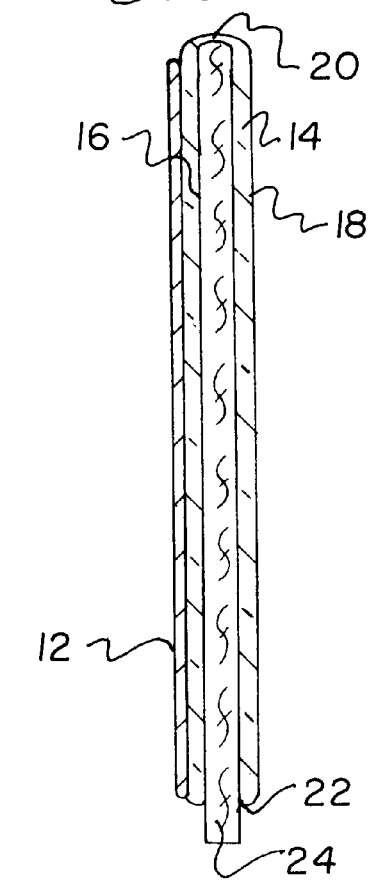
FIG. 4 is a cross-sectional view of the present invention.

Next provided is a thin elongated transparent sleeve 14 having a rectangular configuration and a length of about 9–12 inches. Such sleeve is preferably constructed from a thin transparent plastic such as cellophane. As shown in FIGS. 2 & 4, the sleeve is formed of a front face 16, a rear face 18, a top closed end 20 and a bottom open end 22. The transparent sleeve is coupled to an inner surface of the front portion of the brief in a vertical orientation. In such orientation, the top closed end is extended above the top opening by a length no less than $\frac{1}{20}$ of the total length of the sleeve. The bottom end of the sleeve extends downwardly and terminates at the crotch portion. In an alternate embodiment, the sleeve is integrally formed with the moisture absorbing material. In yet another alternate embodiment, as shown in FIG. 3, a portion of the front face of the sleeve is equipped with an adhesive lining 21 and is adapted to be retrofitted to an existing brief. The adhesive is ideally equipped with a waxed paper removable backing 23 for preserving the adhesive when not in use.

Finally, a moisture indicator strip 24 is provided having a rectangular configuration. The strip is preferably constructed from litmus paper. As shown in FIGS. 2 & 4, the moisture indicator strip is situated within the transparent sleeve such that a top end thereof is situated coincident with the top closed end of the transparent sleeve and a bottom end thereof extends through the bottom opening of the transparent sleeve. It is imperative that the bottom end of the strip reside in communication with the moisture absorbing material of the crotch portion of the brief. By this structure, the strip is adapted to change color upon the detection of moisture. It should be noted that a length of a portion of the strip that changes color is a function of the amount of moisture absorbed by the brief, as dictated by capillary action. As such, when the moisture within the brief has reached a predetermined amount, a change in color will be apparent at the top end of the moisture indicator strip.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An incontinent brief moisture indicator adapted for use with a brief formed of a moisture absorbing material and including a top waist opening and a pair leg openings each lined with a peripheral elastic seam, the brief having a front portion, a rear portion, and a crotch portion, the incontinent brief moisture indicator comprising:

a thin elongated cellophane transparent sleeve having a rectangular configuration with a front face, a rear face, a top closed end and a bottom open end, the transparent sleeve coupled to an inner surface of the front portion of the brief in a vertical orientation with the top closed end situated above and beyond the top opening a distance at least 1/20 a total length of the sleeve and the bottom end extending downwardly and terminating at the crotch portion, wherein the sleeve has a length of about 9–12 inches;

a moisture indicator strip having a rectangular configuration and constructed from litmus paper, the moisture indicator strip situated within the transparent sleeve such that a top end thereof is situated coincident with the top closed end of the transparent sleeve and a bottom end thereof extends through the bottom opening of the transparent sleeve and is situated in communication with the moisture absorbing material of the crotch portion of the brief, whereby the strip is adapted to change color upon the detection of moisture wherein a length of a portion of the strip that changes color is a function of the amount of moisture absorbed by the brief.

2. The incontinent brief moisture indicator as set forth in claim 1 wherein the transparent sleeve is mountable to the inner surface of the front portion of the brief via adhesive.

* * * * *